US011717275B2

(12) United States Patent
Belsky et al.

(10) Patent No.: US 11,717,275 B2
(45) Date of Patent: Aug. 8, 2023

(54) NEEDLE-HANDLING DEVICE

(71) Applicant: ONEPASS MEDICAL, Katzrin (IL)

(72) Inventors: Ziv Belsky, Haifa (IL); Jesse Lachter, Haifa (IL); Gilad Hizkiyahu, Givat Ela (IL)

(73) Assignee: ONEPASS MEDICAL, Katarin (IL)

( * ) Notice: Subject to any disclaimer, the term of this patent is extended or adjusted under 35 U.S.C. 154(b) by 310 days.

(21) Appl. No.: 17/113,643

(22) Filed: Dec. 7, 2020

(65) Prior Publication Data

US 2021/0145419 A1    May 20, 2021

Related U.S. Application Data

(62) Division of application No. 15/757,622, filed as application No. PCT/IL2016/050971 on Sep. 4, 2016, now Pat. No. 10,856,857.

(Continued)

(51) Int. Cl.
  *A61B 10/04* (2006.01)
  *A61B 10/02* (2006.01)
(52) U.S. Cl.
  CPC ...... *A61B 10/04* (2013.01); *A61B 2010/0225* (2013.01); *A61B 2010/045* (2013.01)
(58) Field of Classification Search
  CPC ........ A61B 10/02–06; A61M 25/0084; A61M 2025/0085–0095
  See application file for complete search history.

(56) References Cited

U.S. PATENT DOCUMENTS 5,409,012 A   4/1995 Sahatjian
5,415,182 A   5/1995 Chin et al.
(Continued)

FOREIGN PATENT DOCUMENTS

EP    0450886 A1    10/1991
ES    2617871 T3 *  6/2017    ......... A61B 17/7097
(Continued)

OTHER PUBLICATIONS

PCT Preliminary Report on Patentability for International Application No. PCT/IL2016/050971 dated Mar. 6, 2018, 12 pp.
(Continued)

*Primary Examiner* — Kaylee R Wilson
*Assistant Examiner* — Raymond P Dulman
(74) *Attorney, Agent, or Firm* — The Roy Gross Law Firm, LLC; Roy Gross

(57) ABSTRACT

Apparatus, comprising: a sheath (22), advanceable through an endoscope (10), and having distal openings comprising a first opening (30a) and a plurality of second openings (30b) surrounding the first opening; a housing (24), coupled to a proximal portion of the sheath; a first needle (28a), extending through the housing and sheath toward the first opening; a plurality of second needles (28b), extending through the housing and sheath toward a respective second opening; a first handle (26a), slidably coupled to the housing along an axis such that the first needle slides through the sheath and a distal tip of the first needle moves with respect to the first opening; and a second handle (26b), slidably coupled to the housing along a different axis such that the second needles slide through the sheath and a distal tip of each second needle moves with respect to its respective second opening.

5 Claims, 4 Drawing Sheets

Related U.S. Application Data

(60) Provisional application No. 62/215,003, filed on Sep. 6, 2015.

(56) References Cited

U.S. PATENT DOCUMENTS

| | | |
|---|---|---|
| 2003/0195436 A1 | 10/2003 | Van Bladel et al. |
| 2004/0054363 A1* | 3/2004 | Vaska ............... A61B 17/22012 |
| | | 606/41 |
| 2004/0068242 A1 | 4/2004 | McGuckin |
| 2004/0260274 A1 | 12/2004 | Hardin et al. |
| 2005/0228312 A1 | 10/2005 | Surti |
| 2006/0116605 A1 | 6/2006 | Nakao |
| 2006/0167416 A1 | 7/2006 | Mathis et al. |
| 2007/0162061 A1 | 7/2007 | Way et al. |
| 2010/0298736 A1 | 11/2010 | Levy |
| 2011/0130680 A1 | 6/2011 | Dahlstrand |
| 2012/0010527 A1 | 1/2012 | Sundheimer et al. |
| 2013/0030323 A1* | 1/2013 | Smith ................ A61B 10/0275 |
| | | 600/567 |
| 2014/0005478 A1* | 1/2014 | Kennedy, II ........... A61B 10/04 |
| | | 600/114 |
| 2015/0087994 A1 | 3/2015 | Matsuno et al. |
| 2016/0000415 A1 | 1/2016 | Belsky et al. |

FOREIGN PATENT DOCUMENTS

| | | |
|---|---|---|
| WO | 0033909 A1 | 6/2000 |
| WO | 0064526 A1 | 11/2000 |
| WO | 2010014034 A1 | 2/2010 |
| WO | 2014136045 A1 | 9/2014 |
| WO | 2017037720 A1 | 3/2017 |

OTHER PUBLICATIONS

PCT Search Report for International Application No. PCT/IL2016/050971 dated Feb. 3, 2017, 7 pp.
PCT Written Opinion for International Application No. PCT/IL2016/050971 dated Feb. 3, 2017, 11 pp.
PCT Invitation to Pay Additional Fees for International Application No. PCT/IL2016/050971 dated Dec. 2, 2016, 8 pp.
LeBlanc et al. (2004) Optimal number of EUS-guided fine needle passes needed to obtain a correct diagnosis.
An Office Action dated Oct. 2, 2019 for U.S. Appl. No. 14/772,364, 21 pp.

* cited by examiner

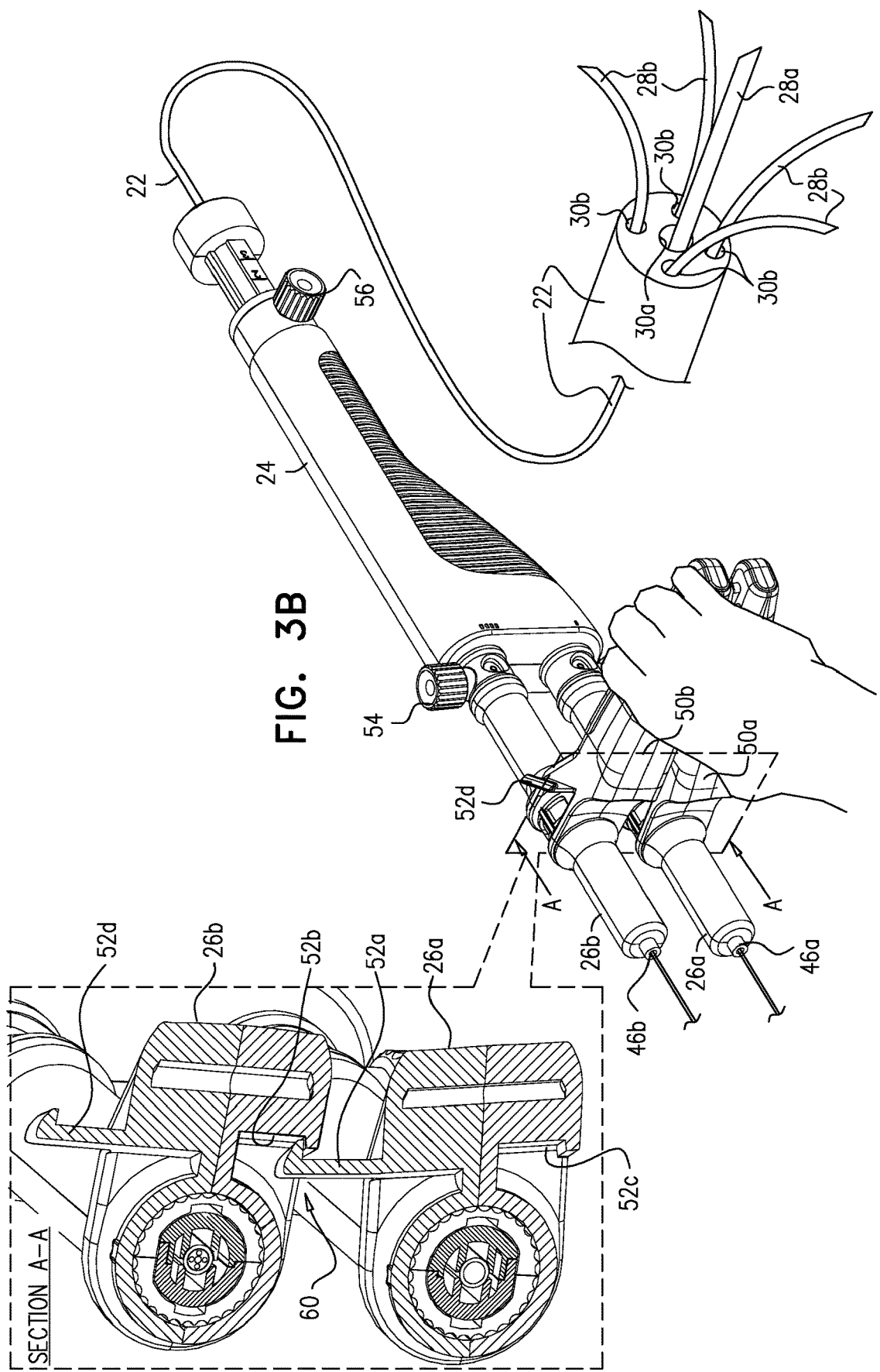

NEEDLE-HANDLING DEVICE

CROSS-REFERENCES TO RELATED APPLICATIONS

The present application is a divisional of U.S. patent application Ser. No. 15/757,622, filed Mar. 5, 2018 and entitled "NEEDLE-HANDLING DEVICE", which is a National Phase of PCT Patent Application No. PCT/IL2016/050971 to Belsky et al., filed Sep. 4, 2016, and entitled "NEEDLE-HANDLING DEVICE", which published as WO 2017/037720, and which claims priority to U.S. Provisional Patent Application No. 62/215,003 to Belsky et al., filed Sep. 6, 2015, and entitled "NEEDLE-HANDLING DEVICE", which is incorporated herein by reference.

The present application is related to U.S. patent application Ser. No. 14/772,364 to Belsky et al., which published as US 2016/0000415, and which is the US National Phase of PCT application IB2014/059420 to Belsky et al., filed Mar. 4, 2014, entitled "Multiple-tissue FNA sampling," which published as WO 2014/136045, both of which are incorporated herein by reference.

FIELD OF THE INVENTION

Some applications of the present invention relate in general to tissue sampling. More specifically, some applications of the present invention relate to tissue-sampling using Fine Needle Aspiration (FNA).

BACKGROUND OF THE INVENTION

Tissue/fluid sampling (e.g., biopsying) is used in many medical fields, e.g., to help in diagnosing of conditions. Physicians (e.g., gastroenterologists) sometimes use an endoscope when performing a biopsy, e.g., in order to sample tissue that cannot easily be reached percutaneously, or to which the physician does not have line-of-sight. Fine-needle aspiration biopsy (FNAB, FNA or NAB), or fine-needle aspiration cytology (FNAC), is a common diagnostic procedure used to investigate superficial lumps or masses. A fine needle is used to obtain a small sample of tissue; sufficient for cytology examination. EUS-FNA is fine needle aspiration during endoscopic ultrasound, using an ultrasound equipped endoscope to navigate to and identify the tissue (e.g., a lesion), and to guide a needle into the tissue. It is often necessary to take multiple samples in order to increase diagnostic accuracy, since a single sample may not represent the entirety of the tissue or lesion from which the sample is extracted.

SUMMARY OF THE INVENTION

A device is provided for facilitating tissue sampling using Fine Needle Aspiration (FNA). At a distal end of the device, multiple needles are extendible, and are disposed such that a first needle is surrounded by a plurality of other needles. At a proximal end of the device, the first needle is spatially separated from the plurality of other needles, facilitating independent movement of the first needle (e.g., using a separate handle), and/or independent application of suction to the first needle (e.g., via a separate port).

For some applications, handles used to independently move (i) the first needle, and (ii) the plurality of other needles, are lockable, so as to facilitate linked movement of the first and other needles.

There is therefore provided, in accordance with an application of the present invention, apparatus, for use with an endoscope, the apparatus including: a flexible sheath, shaped to be advanced through a working channel of the endoscope, and shaped to define a plurality of openings at a distal end of the flexible sheath, the plurality of openings including a first opening, and a plurality of second openings surrounding the first opening; a housing, coupled to a proximal portion of the sheath; an elongate first needle, extending distally through the housing and through the sheath toward the first opening; a plurality of elongate second needles, each extending distally through the housing and through the sheath toward a respective second opening of the plurality of second openings; a first needle-control handle, attached to the first needle, slidably coupled to the housing along a first axis, and slidable with respect to the housing such that sliding of the first needle-control handle slides the first needle through the sheath such that a distal tip of the first needle moves with respect to the first opening; and a second needle-control handle, attached to the plurality of second needles, slidably coupled to the housing along a second different axis, and slidable with respect to the housing such that sliding of the second needle-control handle slides the plurality of second needles through the sheath such that a distal tip of each second needle moves with respect to a respective second opening of the plurality of second openings.

In an application, the apparatus is configured such that: a distance slid by the first needle-control handle with respect to the housing is equal to a distance moved by the tip of the first needle with respect to the first opening, and a distance slid by the second needle-control handle with respect to the housing is equal to a distance moved, by the tip of each second needle of the plurality of second needles, with respect to the respective second opening of the plurality of second openings.

In an application: the sheath is shaped to define (i) a first needle channel that extends through the sheath and opens to the first opening, and (ii) a plurality of second needle channels that extends through the sheath and surrounds the first needle channel, each second needle channel of the plurality of second needle channels opening to a respective second opening of the plurality of second openings, the first needle is disposed in the first needle channel, and each second needle of the plurality of second needles is disposed in a respective second needle channel of the plurality of second needle channels.

In an application, the first axis is parallel to the second axis.

In an application, the first and second axes are parallel, and are 1-10 cm apart.

In an application, the first needle-control handle is slidable along the first axis into the housing at a first site of the housing, and the second needle-control handle is slidable along the second axis into the housing at a second site of the housing that is at least 2 cm from the first site.

In an application, the first needle-control handle is slidably coupled to the housing such that sliding of the first needle-control handle distally with respect to the housing slides the first needle distally out of the first opening, and the second needle-control handle is slidably coupled to the housing such that sliding of the second needle-control handle distally with respect to the housing slides each needle of the plurality of second needles distally out of a respective opening of the plurality of second openings.

There is further provided, in accordance with an application of the present invention, apparatus, including: a sheath, shaped to define a plurality of openings at a distal end of the sheath, the plurality of openings including a first opening, and a plurality of second openings surrounding the first opening; an elongate first needle, extending through the sheath toward the first opening; a plurality of elongate second needles, extending through the sheath toward the plurality of second openings; a first aspirator port, in fluid communication with the first needle; and a second aspirator port, in fluid communication with at least one of the second needles, a center of the second aspirator port being spaced by at least 1 cm from a center of the first aspirator port.

In an application, the second aspirator port is in fluid communication with all the second needles of the plurality of second needles.

In an application, the apparatus is for use with an endoscope, and the sheath is flexible and shaped to be advanced through a working channel of the endoscope.

There is further provided, in accordance with an application of the present invention, apparatus, including: a sheath; a housing, coupled to a proximal portion of the sheath; an elongate first needle, extending through the housing and through the sheath; a plurality of elongate second needles, extending through the housing and through the sheath; a first needle-control handle: attached to the first needle, having a first hand-grip, and slidably coupled to the housing, such that sliding of the first needle-control handle slides the first needle through the sheath; and a second needle-control handle: attached to the plurality of second needles, having a second hand-grip, slidably coupled to the housing, such that sliding of the second needle-control handle slides the plurality of second needles through the sheath, and rotatable with respect to the housing such that: in a first rotational position, the first and second hand-grips are graspable independently and simultaneously by separate hands of a human operator, and in a second rotational position, the first and second hand-grips (i) are closer together than in the first rotational position, and are graspable simultaneously by a single hand of the human operator.

In an application, in the second rotational position, the first and second hand-grips mate to define a single unified hand-grip.

In an application, the apparatus is for use with an endoscope, and the sheath is flexible and shaped to be advanced through a working channel of the endoscope.

There is further provided, in accordance with an application of the present invention, apparatus, including: a sheath; a housing, coupled to a proximal portion of the sheath; an elongate first needle, extending through the housing and through the sheath; a plurality of elongate second needles, extending through the housing and through the sheath; a first needle-control handle: attached to the first needle, having a first hand-grip, and slidably coupled to the housing, such that sliding of the first needle-control handle slides the first needle through the sheath; and a second needle-control handle: attached to the plurality of second needles, having a second hand-grip, slidably coupled to the housing, such that sliding of the second needle-control handle slides the plurality of second needles through the sheath, having a first state in which the first needle-control handle is slidable to slide the first needle through the sheath without causing the plurality of second needles to slide through the sheath, and having a second state in which sliding of the first needle-control handle causes the plurality of second needles to slide through the sheath.

In an application, the apparatus includes a lock, and locking of the lock moves the apparatus from the first state into the second state.

In an application, the apparatus is for use with an endoscope, and the sheath is flexible and shaped to be advanced through a working channel of the endoscope.

In an application, a needle-control handle selected from the group consisting of: the first needle-control handle and the second needle-control handle is rotatable with respect to the housing such that: in a first rotational position of the selected needle-control handle, the apparatus is in the first state, and in a second rotational position of the selected needle-control handle, the apparatus is in the second state.

In an application, the first and second needle-control handles define respective mating surfaces that mate when the selected needle-control handle is in the second rotational position.

The present invention will be more fully understood from the following detailed description of applications thereof, taken together with the drawings, in which:

BRIEF DESCRIPTION OF THE DRAWINGS

FIGS. 3A-B are schematic illustrations, in perspective view, showing use of the device in respective states thereof, in accordance with some applications of the invention.

DETAILED DESCRIPTION OF EMBODIMENTS

Figure 1:
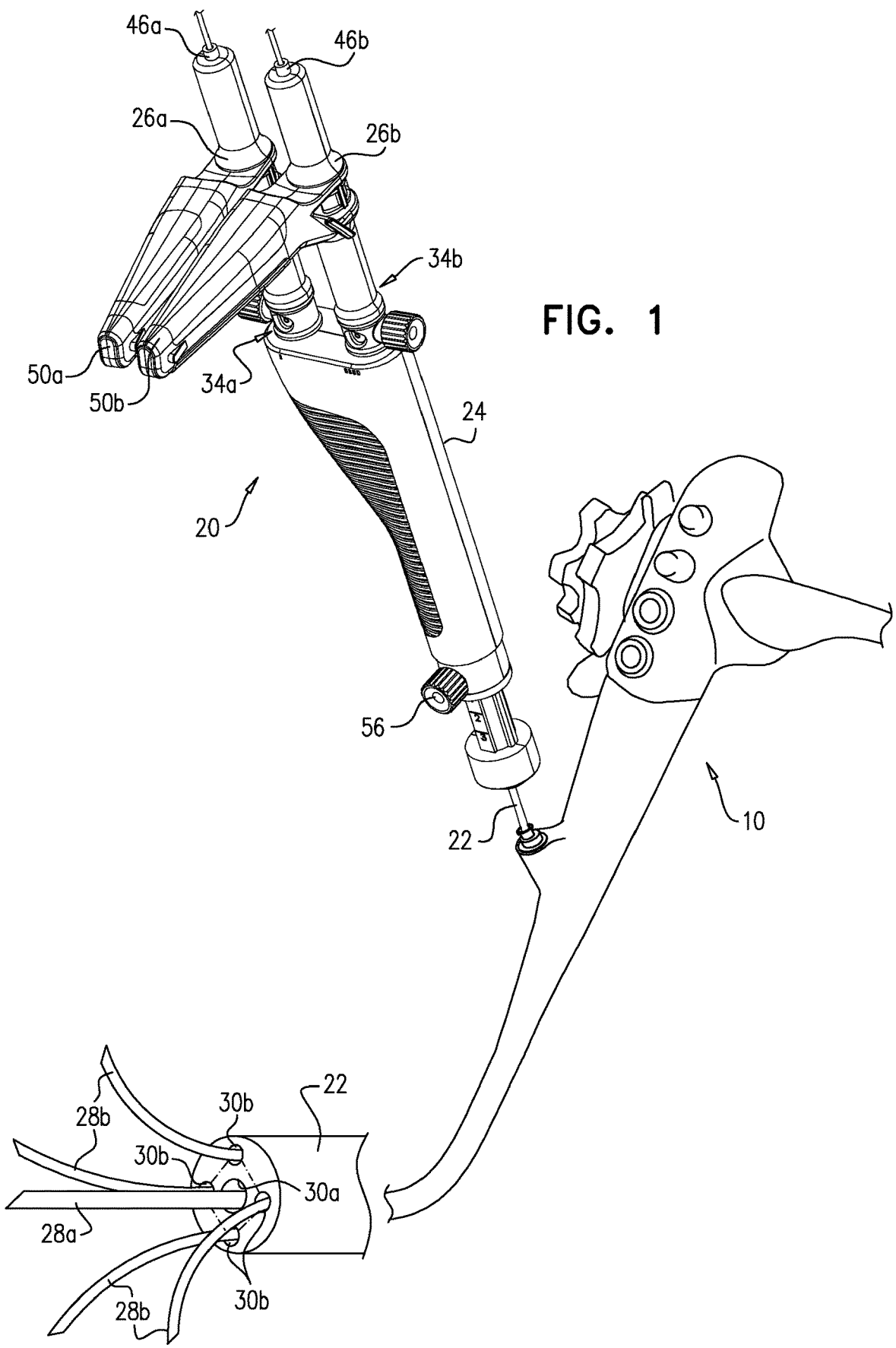
FIG. 1 is a schematic illustration of a device and a guiding tool, in accordance with some applications of the invention.
Figure 2:
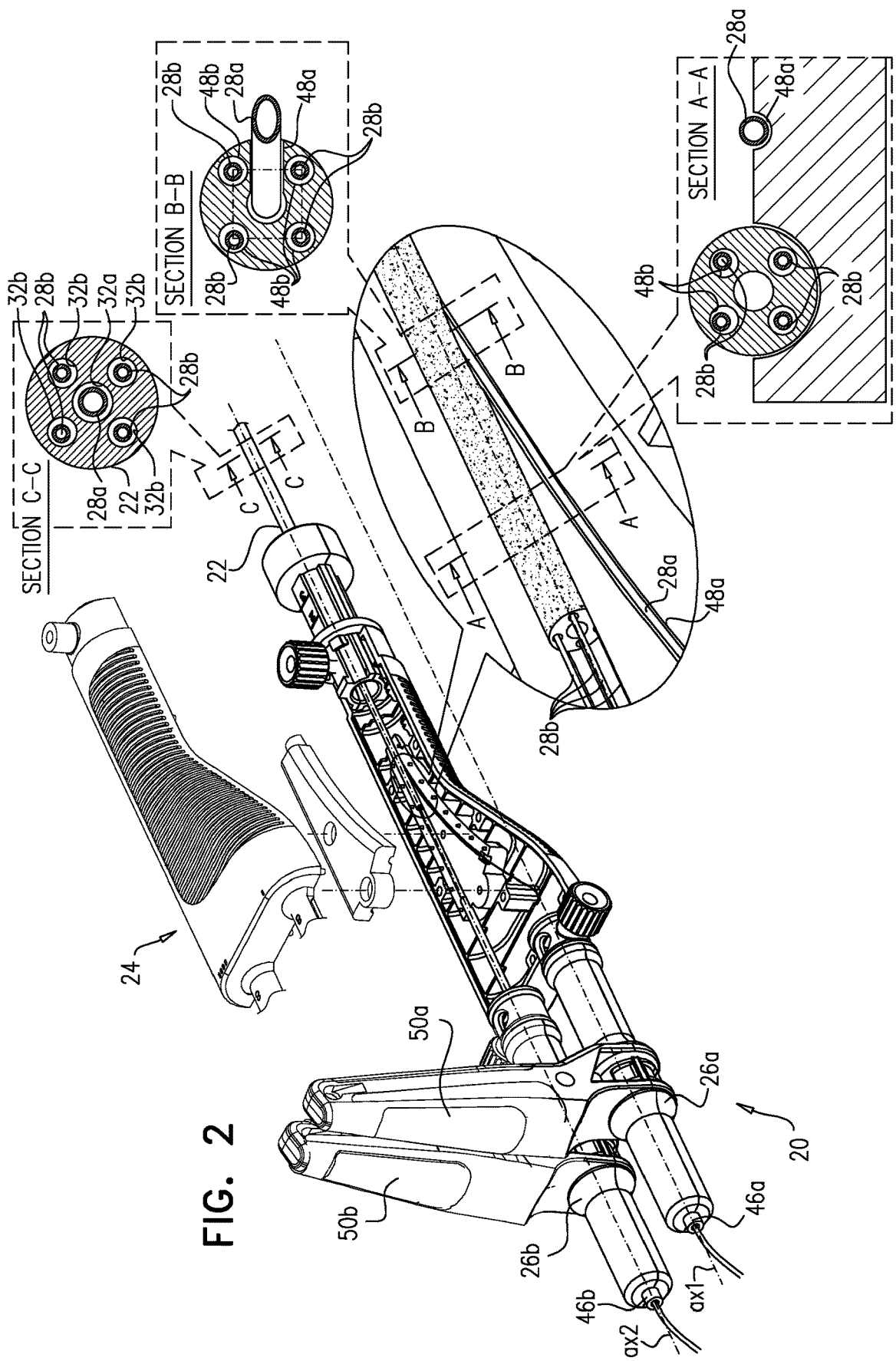
FIG. 2 is a schematic illustration, in perspective and partially-exploded view, of the device, in accordance with some applications of the invention.
Figure 3A:
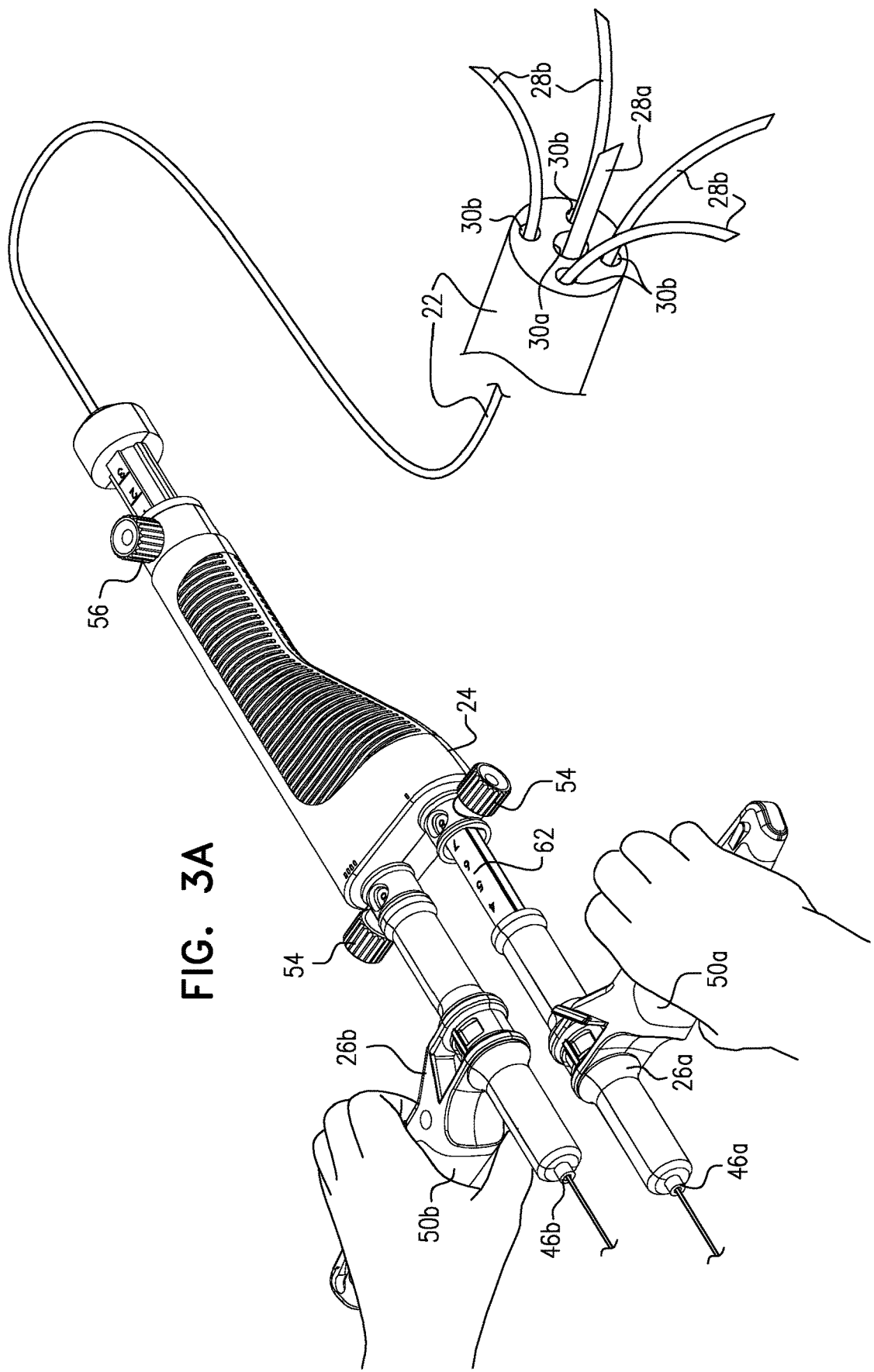

Reference is made to FIGS. 1, 2, and 3A-B, which are schematic illustrations of a device 20, in accordance with some applications of the invention. Device 20 is used for obtaining one or more tissue samples (e.g., biopsy samples) in a fine-needle aspiration biopsy (FNAB) procedure, and is typically advanced through a guiding tool (such as an ultrasonic endoscope) in an FNA procedure such as an EUS-FNA procedure. FIG. 1 is a perspective view of device 20 being used with a guiding tool 10, such as an endoscope, e.g., an ultrasonic endoscope. Device 20 is typically used with such a guiding tool, but may alternatively be used without such a guiding tool (e.g., by being manually guided). FIG. 2 is a perspective view of device 20, including an exploded view of housing 24, in accordance with some applications of the invention. FIGS. 3A-B are perspective views of device 20, showing use of the device in respective states thereof, in accordance with some applications of the invention.

Device 20 comprises a sheath 22, a housing 24 coupled to a proximal portion of the sheath, a first needle-control handle 26a, and a second needle control handle 26b.

Sheath 22 defines a plurality of openings 30 at a distal end thereof. The plurality of openings 30 comprises a first opening 30a, and a plurality of second openings 30b surrounding opening 30a. It is to be noted that, in this context, the term "surrounding" (including the specification and the claims) means that if one were to draw straight lines between the center of each opening 30b and the centers of its nearest neighbors, the center of opening 30a would be disposed within the resulting polygon (e.g., the quadrilateral shape drawn in broken lines in FIG. 1). (Thus, for some applications, opening 30a may be disposed on the edge of the resulting polygon, and may even extend some way outside of the polygon.)

It is to be noted that, for clarity, the distal portion of tool 10 is not shown in FIG. 1.

Handle 26a is slidably coupled to housing 24 along a first axis ax1, and handle 26b is slidably coupled to housing 24 along a second axis ax2. Handle 26a is attached to a first elongate needle 28a, such that sliding of handle 26a with respect to housing 24 (along axis ax1) slides needle 28a through sheath 22, such that a distal tip of the needle moves with respect to opening 30a (e.g., the tip moves through the opening, such as out of the opening). Handle 26b is attached to a plurality of second elongate needles 28b, such that sliding of handle 26b with respect to housing 24 (along axis ax2) slides needles 28b through sheath 22, such that a distal tip of each needle 28b moves with respect to a respective opening 30b (e.g., the tip moves through the respective opening, such as out of the respective opening).

Although needle 28a is described and shown as being a single needle, for some applications needle 28 is a plurality of needles, mutatis mutandis.

FNA needles are known in the art. An FNA needle is a fine hollow needle (e.g., 19 gauge or smaller, and typically 22-25 gauge), used to obtain a sample from a tissue. Typically, an FNA needle has a sharpened tip. Typically, needles 28a and 28b are long (e.g., 100-200 cm long, such as 145-190 cm long) and flexible. Typically, sheath 22 is also flexible, and is shaped to be advanced through a working channel of guiding tool 10. For example, tool 10 may be a steerable ultrasonic endoscope, and sheath 22 may be advanceable through a working channel of the endoscope. For example, tool 10 and device 20 may be advanced into the gastrointestinal tract, and used to obtain a sample of a tissue of the gastrointestinal tract, or tissue proximal to the gastrointestinal tract.

Alternatively, sheath 22 may be rigid, and/or tool 10 may be a rigid trocar. For some applications, sheath 22 may be used without tool 10.

Needle 28a (or at least a distal portion thereof) is typically biased to be straight. That is, in the absence of an external force, the distal portion of needle 28a is typically straight. Therefore when disposed outside of opening 30a, the distal portion of needle 28a typically extends straight out of sheath 22. Each needles 28b (or at least a distal portion thereof) is typically biased to be bent. That is, in the absence of an external force, the distal portion of each needle 28b is typically bent. Therefore when disposed outside of opening 30b, the distal portion of each needle 28b curves. Needles 28b are typically rotationally oriented such that when exposed from the distal end of sheath 22, the distal ends of needles 28b diverge outward from needle 28. It is hypothesized that this arrangement (i) results in needles 28b entering the tissue at a nonzero angle with respect to needle 28a, and therefore (ii) facilitates sampling of tissue over a wider area compared to using a single needle. Each needle 28b is hypothesized to reach a different part of the tissue from that reached by the other needles 28b, and from that reached by needle 28a. Device 20 facilitates control of the position of, and suction through, needles 28b independently of that of needle 28a (as described in more detail hereinbelow). If the physician desires (e.g., in a particular case), needle 28a may be used without using (e.g., without advancing) needles 28b (or vice versa). For some applications, needles 28b are of higher gauge than is needle 28a.

Typically, sheath 22 defines a plurality of needle channels 32 that extend through (i.e., along) the sheath. A first needle channel 32a opens to opening 30a, and a plurality of second needle channels 32b open to respective openings 30b. Needle 28a is disposed in channel 32a, and needles 28b are disposed in respective channels 32b. Typically, channels 32b surround channel 32a along at least the distal half of sheath 22 (e.g., along at least the distal 75 percent of sheath 22, such as along at least the distal 90 percent of sheath 22). For some applications, channels 32b surround channel 32a along the entire of sheath 22.

Typically, sheath 22 has an external diameter of 2.5-3 mm (e.g., 2.7 mm), needle 28a is 22 gauge, and needles 28b are 25 gauge.

For some applications, handle 26a is slidable along axis ax1 into housing 24 at a first site 34a, and handle 26b is slidable along axis ax2 into housing 24 at a second site 34b that is at least 1 cm and/or less than 10 cm (e.g., 1-10 cm, e.g., 2-8 cm, e.g., 4-6 cm, such as about 5 cm) from site 34a. For some applications, axes ax1 and ax2 are parallel. For some such applications, axes ax1 and ax2 are at least 1 cm and/or less than 10 cm (e.g., 1-10 cm, e.g., 2-8 cm, e.g., 4-6 cm, such as about 5 cm) apart.

Typically, device 20 comprises a plurality of aspirator ports 46. A first aspirator port 46a is in fluid communication with needle 28a, and a second aspirator port 46b is in fluid communication with at least one of needles 28b (e.g., with all of needles 28b). When device 20 is used to obtain a biopsy sample, suction is typically applied via the ports, e.g., similarly to the use of suction in existing FNA biopsy procedures. Port 46a is typically coupled to handle 26a, and port 46b is typically coupled to handle 26b. Ports 46a and 46b (i.e., the centers thereof) are spatially separated (e.g., laterally), e.g., by at least 0.5 cm and/or less than 20 cm (e.g., 0.5-20 cm, such as 1-10 cm, such as 1-5 cm).

For some applications, each port 46 comprises a standard medical fitting, such as a Luer-type lock.

The distances between handles 26, ports 46 and axes ax1 and ax2 are typically (i) sufficiently large that ports 46 are independently accessible by separate suction devices (e.g., syringes), and (ii) sufficiently small that the handles may placed together and/or locked together, as described hereinbelow.

An interesting aspect of device 20 is that (a) at a distal portion of the device (e.g., at the distal end of sheath 22), needles 28a and 28b are disposed together, e.g., with needle 28a surrounded by needles 28b (e.g., see section C-C of FIG. 2), which is hypothesized by the inventors to be advantageous for multiple-needle FNA, but (b) at a proximal portion of the device needles 28a and 28b are spatially (e.g., laterally) separated (i.e., needle 28a is not surrounded by needles 28b) (as shown in section A-A of FIG. 2). This spatial separation of needles 28a and 28b facilitates:

(i) handles 26a and 26b being spatially (e.g., laterally) separated and/or being slidable along different (e.g., spatially separated) axes, thereby providing independent movement of needles 28b from needle 28a using different handles; and (ii) spatial (e.g., lateral) separation of ports 46a and 46b, thereby facilitating application of suction to each port independently.

Thus at some point between the proximal end and the distal end of device 20, needle 28a becomes surrounded by needles 28b. Typically, this occurs within housing 24, as is shown in section B-B of FIG. 2. For example, lines drawn between the centers of needles 28b may define a polygon (e.g., the quadrilateral shape drawn in broken lines in section B-B of FIG. 2), both proximally and distally to this point, and progressively distal portions of needle 28a become progressively closer to the polygon, until the centre of needle 28a is disposed within the polygon. (Thus, for some applications, even at distal portions of device 20, needle 28a may be disposed on the edge of the resulting polygon, and may even extend some way outside of the polygon.)

Typically, these described paths of needles 28*a* and 28*b* are provided by housing 24, which defines a plurality of ducts 48 through which the needles extend. For example, needle 28*a* may extend through a first duct 48*a*, and needles 28*b* may extend through respective second ducts 48*b*, and progressively distal portions of duct 48*a* may become progressively closer to ducts 48*b*, until duct 48*a* is surrounded by ducts 48*b* (as shown in section B-B of FIG. 2).

For some applications, at the place in which needle 28*a* passes between two needles 28*b* in order to become surrounded by needles 28*b* (e.g., at the location of section B-B of FIG. 2) the two needles 28*b* are slightly further apart than elsewhere, in order to provide passage for needle 28*a*. For some such applications, at that place needle 28*a* and/or needles 28*b* are not disposed within snug-fitting ducts. For example, housing 24 may define a relatively wide chamber at that place, through which the needles pass.

The ability to apply suction independently advantageously facilitates the physician deciding, even after having advanced sheath 22 into the body of the subject, whether to use both needle 28*a* and needles 28*b*, or just one or the other type of needle. For example, if only a single suction port were provided, if the physician were to decide to use only needle 28*a*, suction through the single suction port would nevertheless be applied to needles 28*b* (still within sheath 22). This may adversely affect the suction that reaches needle 28*a*, may apply suction to undesired tissue sites (e.g., immediately outside of openings 30*b*), and/or may cause contamination of the sample obtained with needle 28*a*. For some applications the ability to apply suction independently to needle 28*a* and needles 28*b* is also advantageous if the needles are of different gauges, e.g., because different degrees of suction may be needed to draw sample into the needles.

For some applications, ducts 48*a* and 48*b* are in fluid communication with and/or are continuous with channels 32*a* and 32*b*, respectively. For some applications, proximal portions of channels 32*b* serve as and/or define respective ducts 48*b*. For example, a proximal portion of sheath 22 may be disposed inside housing 24.

As described hereinabove, device 20 facilitates control (e.g., distal and proximal sliding) of needles 28*b* from needle 28*a*. This is shown in FIG. 3A, in which handle 26*b* has been advanced further distally than has handle 26*a*, and needles 28*b* thereby have moved with respect to openings 30*b* further than needle 28*a* has moved with respect to opening 30*a*. Typically device 20 is calibrated such that this results in needles 28*b* extending out of openings 30*b* further than needle 28*a* extends out of opening 30*a* (as shown in FIG. 3A), although it is to be noted that by providing needles of different lengths, a different result may be achieved.

Typically, the distance slid by handle 26*a* is equal to the distance moved by the tip of needle 28*a*, and the distance slid by handle 26*b* is equal to the distance moved by the tip of each needle 28*b*. This is typically facilitated by the provision of a separate duct 48 and channel 32 for each needle 28, and by each needle 28 fitting snugly within its respective duct and channel, so as to prevent buckling of the needles.

As is apparent from FIG. 2, for some applications the path followed by needle 28*a* is longer than the path followed by each needle 28*b*. For some such applications, needle 28*a* is longer than needles 28*b* in order to compensate for this. However, for some applications, needle 28*a* might not be longer.

As shown in FIGS. 3A-B, handles 26*a* and 26*b* are configured to facilitate the above-described independent movement of needles 28*a* and 28*b*, as well as to facilitate linked movement of the needles. FIG. 3A shows a state of device 20 in which a hand-grip 50 of each handle (e.g., a hand-grip 50*a* of handle 26*a* and a hand-grip 50*b* of handle 26*b*) is graspable independently and simultaneously by separate hands of a human operator. (It is to be noted that, although each handle is graspable by separate hands, the operator may move one handle at a time, using a single hand.)

FIG. 3B shows a state of device 20 in which hand-grips 50*a* and 50*b* are graspable simultaneously by a single hand of the human operator, e.g., by hand-grips 50*a* and 50*b* becoming sufficiently close to define a single unified hand-grip. Typically, handles 26 are transitioned from the state shown in FIG. 3A to the state shown in FIG. 3B by rotation of at least one of the handles. For some applications, and as shown, handle 26*a* is rotatable around axis ax1, and handle 26*b* is rotatable around axis ax2.

In the state shown in FIG. 3A, sliding of handle 26*a* (e.g., by applying an axial pushing or pulling force) causes needle 28*a* to slide through sheath 22 without causing needles 28*b* to slide through the sheath. (This is further facilitated by the provision of a separate duct 48*a* and channel 32*a* for needle 28*a*, which prevent friction or other interaction between needle 28*a* and the other needles.) For some applications, in the state shown in FIG. 3B, sliding of handle 26*a* causes both needle 28*a* and needles 28*b* to slide through sheath 22 (e.g., by the same distance). For example, and as shown in FIG. 3B, handle 26*a* may define a first mating surface 52*a*, and handle 26*b* may define a respective second mating surface 52*b* that mates with mating surface 52*a* when the mating surfaces are brought together (e.g., by rotation of the handles). The pair of mating surfaces 52*a* and 52*b* may therefore define a lock 60. Mating of the mating surfaces (e.g., locking of the lock) results linked movement of handles 26*a* and 26*b*, and therefore results in sliding of both needle 28*a* and needles 28*b* when an axial force is applied to either handle. For some applications, and as shown, a second pair of mating surfaces 52*c* and 52*d* (and thereby a second lock) may be defined by handles 26*a* and 26*b*, such that the handles are lockable in both (i) a first rotational orientation (e.g., the orientation shown in FIG. 3B), and (ii) a second rotational orientation, in which each of the handles is rotated about its axis by about 180 degrees until the handles meet on the opposite side of the device.

Typically, at least one gauge 62 is provided to indicate a distance of advancement of each handle 26 relative to housing 24, thereby indicating a distance of advancement out of sheath 22 of the respective needle(s) 28. Typically, each handle 26 is coupled to a respective handle-advancement limiter 54, which limits the advancement of the respective handle, and thereby limits the distance out of sheath 22 that the respective needle(s) may be advanced. For example, limiter 54 may be lockable at a user-selectable distance along its respective handle 26.

For some applications, device 20 comprises an offset adjuster 56, which is used to compensate for different working-channel lengths of different endoscopes by adjusting the distance through the endoscope that sheath 22 is advanced (e.g., adjusting the effective length of the sheath). Using offset adjuster 56, device 20 may be calibrated for a given endoscope, such that gauge 62 accurately indicates advancement of needle(s) 28 (e.g., the amount of advancement relative to a distal end of the endoscope).

For some applications, device 20 is lockable to endoscope 10, e.g., via a Luer-type lock fitting (not visible in the figures) that mates with a counterpart fitting on the endoscope. Typically, this fitting is coupled to (or defined by) offset adjuster 56.

Typically, device 20 is provided (e.g., packaged) with needles 28 disposed within housing 24 and sheath 22. For some applications, needles 28 are provided separately, and are subsequently introduced into ducts 48 and channels 32, e.g., at the institution in which device 20 will be used, such as by the physician or a technician.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
   a sheath;
   a housing, coupled to a proximal portion of the sheath;
   an elongate first needle, extending through the housing and through the sheath;
   a plurality of elongate second needles, extending through the housing and through the sheath;
   a first needle-control handle:
      attached to the first needle,
      having a first hand-grip, and
      slidably coupled to the housing, such that sliding of the first needle-control handle slides the first needle through the sheath; and
   a second needle-control handle:
      attached to the plurality of second needles,
      having a second hand-grip,
      slidably coupled to the housing, such that sliding of the second needle-control handle slides the plurality of second needles through the sheath,
      wherein the apparatus has a first state in which the first needle-control handle is slidable to slide the first needle through the sheath without causing the plurality of second needles to slide through the sheath, and
      wherein the apparatus has a second state in which sliding of the first needle-control handle causes the plurality of second needles to slide through the sheath.

2. The apparatus according to claim 1, wherein the apparatus comprises a lock, and locking of the lock moves the apparatus from the first state into the second state.

3. The apparatus according to claim 1, wherein the apparatus is for use with an endoscope, and the sheath is flexible and shaped to be advanced through a working channel of the endoscope.

4. The apparatus according to claim 1, wherein a needle-control handle selected from the group consisting of: the first needle-control handle and the second needle-control handle is rotatable with respect to the housing such that:
   in a first rotational position of the selected needle-control handle, the apparatus is in the first state, and
   in a second rotational position of the selected needle-control handle, the apparatus is in the second state.

5. The apparatus according to claim 4, wherein the first and second needle-control handles define respective mating surfaces that mate when the selected needle-control handle is in the second rotational position.

* * * * *